United States Patent [19]
Bondinell et al.

[11] 4,258,049
[45] Mar. 24, 1981

[54] INHIBITING PHENYLETHANOLAMINE N-METHYLTRANSFERASE WITH THIADIAZOLO AND OXADIAZOLOTETRAHYDROISOQUINO-LINES

[75] Inventors: William E. Bondinell, Cherry Hill, N.J.; Gerald R. Girard, Cornwell Heights, Pa.

[73] Assignee: SmithKline Corporation, Philadelphia, Pa.

[21] Appl. No.: 130,662

[22] Filed: Mar. 17, 1980

Related U.S. Application Data

[63] Continuation-in-part of Ser. No. 54,343, Jul. 2, 1979, abandoned.

[51] Int. Cl.³ .................. A61K 31/47; C07D 498/04; C07D 513/04

[52] U.S. Cl. .................. 424/258; 546/83; 546/139; 546/143; 546/146

[58] Field of Search .................. 546/83; 424/258

[56] References Cited

U.S. PATENT DOCUMENTS 3,939,164  2/1976  Kaiser et al. .................. 424/258 X
4,062,961  12/1977  Kaiser et al. .................. 424/258

Primary Examiner—Henry R. Jiles
Assistant Examiner—Richard A. Schwartz
Attorney, Agent, or Firm—Joseph A. Marlino; Richard D. Foggio; Alan D. Lourie

[57] ABSTRACT

Thiadiazolo- and oxadiazolotetrahydroisoquinoline compounds are inhibitors of phenylethanolamine N-methyltransferase.

14 Claims, No Drawings

INHIBITING PHENYLETHANOLAMINE N-METHYLTRANSFERASE WITH THIADIAZOLO AND OXADIAZOLOTETRAHYDROISOQUINOLINES

This application is a continuation-in-part application of Ser. No. 054,343 filed July 2, 1979, now abandoned.

This invention relates to new thiadiazolo- and oxadiazolotetrahydroisoquinoline compounds. These compounds have pharmacological activity, in particular they inhibit the enzyme phenylethanolamine N-methyltransferase.

Epinephrine is a hormone, synthesized in the adrenal medulla, which is released into the blood stream in response to stress and produces profound physiological changes which serve to prepare the animal to cope with the stressor situation. For example, epinephrine produces anxiety, an increase in blood pressure, acceleration of heart rate and increase in cardiac output. These changes are detrimental in individuals with certain disease conditions such as angina pectoris, myocardial infarction and anxiety neuroses.

Phenylethanolamine N-methyltransferase catalyzes the final step in the biosynthesis of epinephrine, that is the transfer of a methyl group from S-adenosylmethionine to norepinephrine to produce epinephrine.

The compounds of this invention inhibit phenylethanolamine N-methyltransferase and thus reduce the formation of epinephrine. They are therefore useful in situations where there is overproduction of epinephrine or where epinephrine production is detrimental.

The compounds of this invention may exist as isomers and it is the intent of this invention to include all possible isomers. These isomers are illustrated by the following formulas:

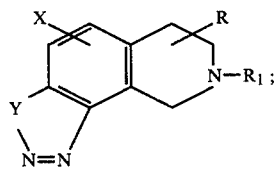

Formula I

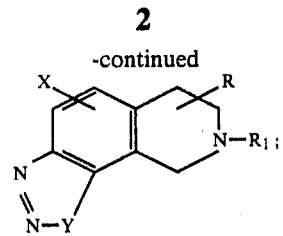

Formula II

Formula III

Formula IV

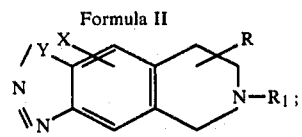

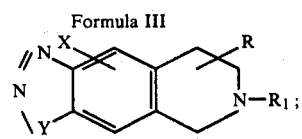

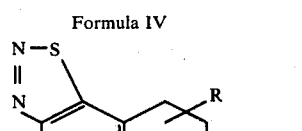

Formula V

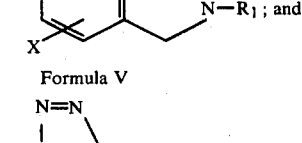

Formula VI in which:
Y is sulfur or oxygen;
when Y is sulfur, X is hydrogen, halogen, or trifluoromethyl and R and $R_1$ are hydrogen or lower alkyl of from one to three carbon atoms;
when Y is oxygen, X, R and $R_1$ are hydrogen; and pharmaceutically acceptable acid addition salts thereof.

Compounds of this invention represented by Formula I, when Y is sulfur R is lower alkyl and X and $R_1$ are hydrogen, are prepared by the following procedure:

Scheme I

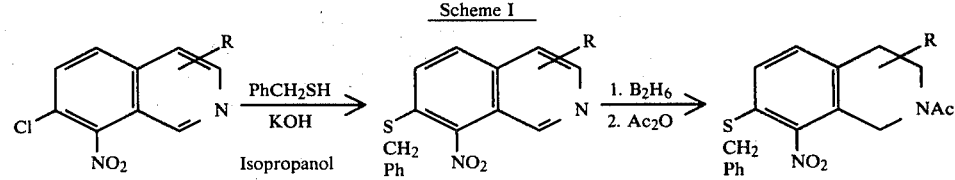

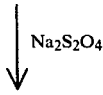

Scheme I
-continued

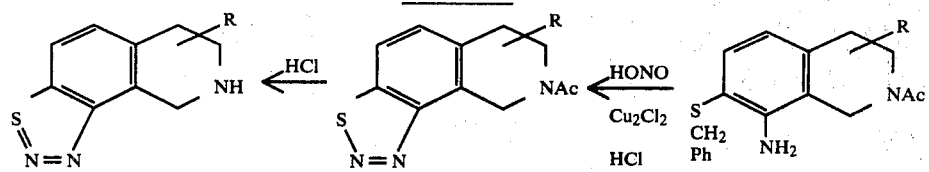

As shown above, the properly substituted 7-chloro-8-nitroisoquinoline is reacted with benzyl mercaptan to yield the corresponding 7-benzylthio derivative. The benzylthio compound is then reduced with, for example, diborane and acylated to the corresponding N-acetyl tetrahydroisoquinoline. The nitro moiety is then reduced to the amine and cyclization is accomplished by diazotizing and treating the diazonium salt with cuprous chloride and hydrochloric acid. The acetyl group is then hydrolyzed.

Compounds of Formulas III or IV where Y is sulfur are prepared from 2-acetyl-6-chloro or 2-acetyl-7-chloro-1,2,3,4-tetrahydroisoquinoline by nitration and treatment with benzyl-mercaptan to yield the respective benzylthio compounds which are further converted by the methods shown in Scheme I, to give the desired thiadiazolo compounds.

Alternatively, compounds of Formulas I or II where Y is sulfur may be made from 8-amino- or 7-aminoisoquinoline, respectively, by treatment with sulfur monochloride to give a dithiazolo compound which is treated with nitrous acid to yield the desired thiadiazolo compound which is reduced, with, for example, sodium cyanoborohydride as disclosed below.

appropriate aldehyde and a reducing agent such as sodium cyanoborohydride.

The trifluoromethyl or halo derivatives may also be made by use of appropriately substituted starting materials and employing the procedures of Scheme II. For example, 7-amino-8-trifluoromethylisoquinoline and 7-amino-8-chloroisoquinoline are converted to 4-trifluoromethyl-[1,2,3]-thiadiazolo-[5,4-g]-5,6,7,8-tetrahydroisoquinoline and 4-chloro-[1,2,3]-thiadiazolo[5,4-g]-5,6,7,8-tetrahydroisoquinoline.

Oxadiazolotetrahydroisoquinolines of Formula I and II, where Y is oxygen, are prepared from 2-acetyl-8(7)-amino-7(8)-chloro-1,2,3,4-tetrahydroisoquinoline and Formulas III and IV are prepared from 2-acetyl-7(6)-amino-6(7)-chloro-1,2,3,4-tetrahydroisoquinoline by diazotization and neutralization of the resulting solution to form the oxadiazolo moiety. The acetyl group is removed by hydrolysis.

The nontoxic pharmaceutically acceptable acid addition salts of the compounds of Formulas I–VI are similarly useful as the free bases. Such salts are easily prepared by methods known to the art. The base is reacted with an organic or inorganic acid in aqueous miscible solvent, such as acetone or ethanol, with isolation of the

Scheme II

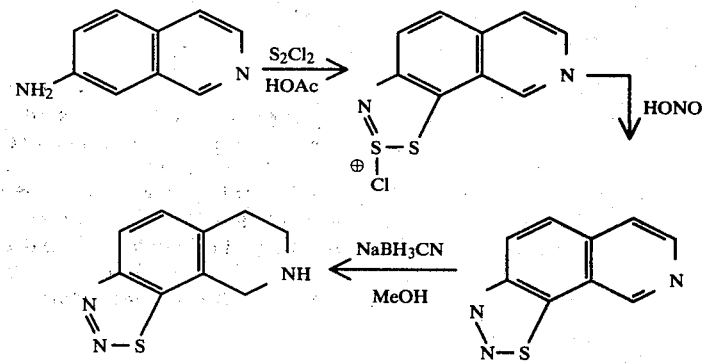

Formula II

Compounds of Formulas V and VI where Y is sulfur are prepared by treating 6-amino- or 5-aminoisoquinoline with sulfur momochloride followed by nitrous acid as shown in Scheme II.

The compounds where X is halogen are prepared by treating 5-amino- or 8-aminoisoquinoline with sulfur monochloride (Scheme II). This results in the introduction of a chloro substituent into the vacant para-position to yield 5-chloro-[1,2,3]thiadiazolo[4,5-f]-6,7,8,9-tetrahydroisoquinoline and 5-chloro-[1,2,3]-thiadiazolo[5,4-h]-6,7,8,9-tetrahydroisoquinoline respectively.

Compounds of Formulas I–VI where $R_1$ is lower alkyl may be made by treatment of the tetrahydroisoquinoline product where $R_1$ is hydrogen with the salt by concentration and cooling or in aqueous immiscible solvent, such as ethyl ether or chloroform, with the desired salt separating directly. Exemplary of the salts which are included in this invention are maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate, citraconate, aspartate, stearate, palmitate, itaconate, glycolate, p-aminobenzoate, glutamate, theophylline acetates, hydrochloride, hydrobromide, sulfate, cyclohexylsulfamate, phosphate and nitrate salts.

The activity of the compounds of Formulas I–VI is demonstrated by inhibition of phenylethanolamine N-methyltransferase in vitro by the assay procedure described by Pendleton and Snow, *Molecular Pharmacology*, 9:718–725 (1973) at various compound concentrations. For example, at concentrations of $1.0 \times 10^{-4}$ and $1.0 \times 10^{-6}$ preferred compounds of this invention, [1,2,3]thiadiazolo[5,4-h]-6,7,8,9-tetrahydroisoquinoline hydrochloride and [1,2,3]thiadiazolo[4,5-h]-6,7,8,9-tetrahydroisoquinoline hydrochloride inhibit phenylethanolamine N-methyltransferase by 99% and 94% and by 99% and 91% respectively.

In addition, the activity of the compounds of this invention is demonstrated in vivo by administration to mice at 50 mg./kg. per day for seven consecutive days. Male mice were dosed orally with either drug or vehicle control on a twice-a-day basis for seven consecutive days. On the morning of the next day they were again dosed and two hours later sacrificed by decapitation. The adrenal glands were then removed and analyzed fluorometrically for both epinephrine and norepinephrine content. A compound is considered active as a PNMT inhibitor if it significantly (at least $p<0.05$) decreases the adrenal epinephrine/norepinephrine ratio (R. G. Pendleton et al., *J. Pharmacol. Exp. Ther.* 190:551–562, 1974 and R. G. Pendleton et al., *J. Pharmacol. Exp. Ther.* 197:623–632, 1976). An above preferred compound of this invention, [1,2,3]thiadiazolo[5,4-h]-6,7,8,9-tetrahydroisoquinoline hydrochloride, significantly lowered the adrenal epinephrine/norepinephrine ratio from $2.4 \pm 0.23$ to $1.3 \pm 0.08$ ($p<0.01$).

The pharmaceutical compositions of this invention to inhibit phenylethanolamine N-methyltransferase comprise a pharmaceutical carrier and, as the active ingredient, a tetrahydroisoquinoline compound of Formulas I–VI. The active ingredient will be present in the compositions of this invention in an effective amount to inhibit phenylethanolamine N-methyltransferase.

Preferably, the compositions of this invention contain the active ingredient of Formula I in an amount of from about 50 mg. to about 1000 mg., advantageously from about 100 mg. to about 500 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of inhibiting phenylethanolamine N-methyltransferase, according to this invention, comprises administering to an animal in an amount sufficient to inhibit phenylethanolamine N-methyltransferase a tetrahydroisoquinoline compound of Formula I–VI.

Preferably, the compounds of Formula I–VI are administered in conventional dosage unit forms prepared by combining an appropriate dose of the compound with standard pharmaceutical carriers.

Preferably, the active ingredient of Formula I–VI will be administered in a daily dosage regimen of from about 100 mg. to about 2000 mg., most preferably from about 200 mg. to about 1000 mg. Advantageously, equal doses will be administered preferably two to three times per day. When the administration is carried out as described above, inhibition of phenylethanolamine N-methyltransferase is produced.

The route of administration of the pharmaceutical compositions of this invention and in accordance with the methods of this invention is internal, either parenteral or preferably oral, in an amount to produce the desired biological activity.

The following examples are not limiting but are illustrative of the compounds of this invention and processes for their preparation.

EXAMPLE 1

A mixture of 0.52 g. (2.5 mmole) of 7-chloro-8-nitroisoquinoline and 0.317 g. (2.56 mmole) of benzyl mercaptan in 5 ml. of degassed isopropanol under argon at 0° C. was treated with 0.16 g. (2.5 mmole) of 86% KOH in 2 ml. of ethanol dropwise over fifteen minutes. The mixture was stirred for one hour at 25° C. and filtered. The collected product was washed with water and ethanol and then dried to yield 7-benzylthio-8-nitroisoquinoline having a melting point of 151°–153° C.

A solution of 15 g. (0.051 mole) of 7-benzylthio-8-nitroisoquinoline in 100 ml. of tetrahydrofuran was added to 210 ml. of 1 M borane-tetrahydrofuran (0.21 mole). The mixture was stirred and refluxed for five hours. Methanol was added and the mixture evaporated in vacuo. The residue was treated with refluxing 12 N HCl for 15 hours, then evaporated to dryness. The resulting solid was recrystallized from methanol-ether to give 7-benzylthio-8-nitro-1,2,3,4-tetrahydroisoquinoline hydrochloride having a melting point of 253° C. with decomposition.

A mixture of 17.5 g. (0.052 mole) of 7-benzylthio-8-nitro-1,2,3,4-tetrahydroisoquinoline hydrochloride, 15 ml. of acetic anhydride and 4.5 g. (0.055 mole) of sodium acetate in 150 ml. of acetic acid was heated on a steam bath for one hour, then evaporated. Water and aqueous ammonia was added to the residue until the mixture was basic. The mixture was extracted with methylene chloride, the extracts combined and washed with water, 10% hydrochloric acid, 5% sodium bicarbonate, dried over sodium sulfate and concentrated. Chromatography of the residue on silica (ethyl acetate) gave 2-acetyl-7-benzylthio-8-nitro-1,2,3,4-tetrahydroisoquinoline, melting point 94°–95° C.

A solution of 1.2 g. (0.0035 mole) of the above 2-acetyl derivative in 15 ml. of ethanol and 10 ml. of water was treated with 4.2 g. (0.23 mole) of sodium hydrosulfite. The mixture was refluxed for three hours, basified with aqueous ammonia and extracted with methylene chloride. The organic extracts were combined, washed with water, dried over sodium sulfate and concentrated to give 2-acetyl-8-amino-7-benzylthio-1,2,3,4-tetrahydroisoquinoline.

To a solution of 1.5 g. (0.0048 mole) of the above 8-amino-tetrahydroisoquinoline derivative in 15 ml. of 12 N hydrochloric acid and 6 ml. of acetic acid at −10° C. under argon was added 0.52 g. (0.0075 mole) of sodium nitrite in 3 ml. of water. The mixture was stirred for five minutes then added rapidly to 2.3 g. of cuprous chloride in 20 ml. of 12 N hydrochloric acid and heated to 60° C. for three hours. The mixture was poured over ice, basified with aqueous ammonia and extracted with methylene chloride. The extracts were combined washed with water, dried and concentrated to give the corresponding diazonium salt. The salt was heated with 2.2 g. of cuprous chloride and 40 ml. of 12 N hydrochloric acid for five hours at 60° C., followed by work-up as above to yield 8-acetyl-[1,2,3]thiadiazolo[5,4-h]-6,7,8,9-tetrahydroisoquinoline having a melting point of 133°–136° C.

A mixture of 0.15 g. (0.0006 mole) of the above thiadiazolo derivative and 5 ml. of 10% hydrochloric acid was refluxed for three hours and evaporated. The residue was dissolved in water, washed with methylene chloride, basified with aqueous ammonia and again extracted with methylene chloride. The methylene chloride extracts were combined, dried and evaporated. The residue was dissolved in methanol, acidified with hydrochloric acid-ether followed by further dilution with ether. The precipitate was recrystallized from methanol-ether to yield [1,2,3]thiadiazolo[5,4-h]-6,7,8,9-tetrahydroisoquinoline hydrochloride having a melting point of 285°–286° C. (dec.).

EXAMPLE 2

A solution of 2.0 g. (0.014 mole) of 7-aminoisoquinoline in 50 ml. of acetic acid was added to 80 ml. of cold sulfur monochloride and stirred for twenty-four hours. The mixture was filtered and the orange solid washed with ether and dried in vacuo to give [1,2,3]dithiazolo[4,5-h]isoquinoline-2-ium chloride hydrochloride, melting point 227°–237° C.

A solution of 2.4 g. (0.009 mole) of the above hydrochloride in 50 ml. of 50% aqueous sulfuric acid was cooled to 0° C. and treated with a solution of 0.97 g. (0.014 mole) of sodium nitrite in 10 ml. of water. The mixture was stirred at 0° C. for two hours, poured into ice water, treated with charcoal, filtered, basified with ammonium hydroxide and extracted with ether. The combined ether extracts were dried, treated with charcoal, filtered and partly concentrated to yield [1,2,3]thiadiazolo[4,5-h]isoquinoline, melting point 150°–153° C.

A solution of 0.5 g. (0.003 mole) of the above isoquinoline in 50 ml. of methanol was treated with 1 g. (0.016 mole) of sodium cyanoborohydride and the resulting solution was stirred for twenty-four hours. The pH was maintained at pH 4 by the addition of methanolic hydrogen chloride. The mixture was then treated with excess methanolic hydrogen chloride and concentrated on a steam bath. The residue was dissolved in water, treated with charcoal, filtered and basified with ammonium hydroxide. The basic solution was extracted with ether and the combined extracts were dried, treated with charcoal and filtered. Treatment with ethereal hydrogen chloride gave [1,2,3]thiadiazolo[4,5-h]-6,7,8,9-tetrahydroisoquinoline hydrochloride, melting point 284°–285° C.

EXAMPLE 3

A solution of 20.9 g. (0.1 mole) of 2-acetyl-7-chloro-1,2,3,4-tetrahydroisoquinoline in 100 ml. of concentrated sulfuric acid is treated with 10 g. (0.1 mole) of potassium nitrate dissolved in 150 ml. of concentrated sulfuric acid. The mixture is stirred for one hour, quenched on ice, made alkaline with ammonium hydroxide and filtered to yield 2-acetyl-7-chloro-6-nitro-1,2,3,4-tetrahydroisoquinoline.

Treatment of the above tetrahydroisoquinoline with benzylmercaptan and following the procedure of Example 1 yields [1,2,3]thiadiazolo[4,5-g]-5,6,7,8-tetrahydroisoquinoline.

EXAMPLE 4

Following the procedures of Example 3 and employing 2-acetyl-6-chloro-1,2,2,4-tetrahydroisoquinoline as a starting material yields 2-acetyl-6-chloro-7-nitro-1,2,3,4-tetrahydroisoquinoline which is converted to [1,2,3]thiadiazolo-[5,4-g]-5,6,7,8-tetrahydroisoquinoline.

EXAMPLE 5

Following the procedure of Example 2, 8-aminoisoquinoline was converted to 5-chloro-[1,2,3]dithiazolo-[5,4-h]isoquinoline-2-ium chloride hydrochloride and then to 5-chloro-[1,2,3]thiadiazolo[5,4-h]isoquinoline, melting point, 225°–227° C.

The above thiadiazoloisoquinoline is reduced with sodium cyanoborohydride also following the procedure of Example 2, to give 5-chloro-[1,2,3]thiadiazolo[5,4-h]-6,7,8,9-tetrahydroisoquinoline.

EXAMPLE 6

2-Acetyl-7-amino-8-chloro-1,2,3,4-tetrahydroisoquinoline (2.2 gm., 0.01 mole) is dissolved in a mixture of 10 ml. of concentrated hydrochloric acid and 20 ml. of water and diazotized by the addition of sodium nitrite (0.7 gm., 0.01 mole) at 3° C. The mixture is stirred for 30 minutes and then treated with sodium carbonate (7.0 gm., 0.065 mole) to a pH of 7. The mixture is extracted with chloroform to give 8-acetyl-[1,2,3]oxadiazolo[4,5-h]-6,7,8,9-tetrahydroisoquinoline on evaporation.

Refluxing with 10% hydrochloric acid, following the procedure of Example 1, gives [1,2,3]oxadiazolo[4,5-h]-6,7,8,9-tetrahydroisoquinoline hydrochloride.

EXAMPLE 7

Following the procedure of Example 6, 2-acetyl-8-amino-7-chloro-1,2,3,4-tetrahydroisoquinoline is converted to [1,2,3]-oxadiazolo[5,4-h]-6,7,8,9-tetrahydroisoquinoline hydrochloride.

EXAMPLE 8

A mixture of 17.3 g. (0.1 mole) of 7-methoxy-4-methylisoquinoline and 100 ml. of 48% hydrobromic acid is refluxed for sixteen hours and evaporated in vacuo. The residue is dissolved in water, neutralized with ammonium hydroxide and filtered to yield 7-hydroxy-4-methylisoquinoline.

A mixture of 15.9 g. (0.1 mole) of 7-hydroxy-4-methylisoquinoline and 41.7 g. (0.125 mole) of triphenylphosphine dichloride is heated to 230° C. for four hours, cooled, and partitioned between chloroform and concentrated hydrochloric acid. The aqueous phase is neutralized with ammonium hydroxide and extracted with chloroform to yield 7-chloro-4-methylisoquinoline.

A mixture of 17.7 g. (0.1 mole) of 7-chloro-4-methylisoquinoline and 100 ml. of concentrated sulfuric acid is treated with 10 g. (0.1 mole) of potassium nitrate dissolved in 150 ml. of concentrated sulfuric acid. The mixture is stirred for one hour, quenched on ice, made alkaline with ammonium hydroxide and filtered to yield 7-chloro-4-methyl-8-nitroisoquinoline.

Following the procedure of Example 1, 7-chloro-4-methyl-8-nitroisoquinoline is converted to 6-methyl-[1,2,3]-thiadiazolo[5,4-h]-6,7,8,9-tetrahydroisoquinoline hydrochloride.

EXAMPLE 9

A solution of 13.6 g. (0.1 mole) of 3-methoxy-benzaldehyde and 10.5 g. (0.1 mole) of aminoacetaldehyde dimethyl acetal in 250 ml. of toluene is refluxed for one hour and water produced in the reaction is collected in a Dean-Stark trap. The resulting solution of 3-methoxy-N-(2,2-dimethoxyethyl)benzylidenamine is added to a solution of (0.2 mole) of methylmagnesium iodide in 250 ml. of ether over 1.5 hours. The mixture is stirred for one hour, cooled and quenched by careful addition of 250 ml. of water. The aqueous phase was filtered through Celite, extracted with 150 ml. of ether and the combined organic phases washed, dried and evaporated to yield 3-methoxy-α-methyl-N-(2,2-dimethoxyethyl)-benzylamine.

A mixture of 23.9 g. (0.1 mole) of 3-methoxy-α-methyl-N-(2,2-dimethoxyethyl)benzylamine in 100 ml. of dry pyridine is stirred, cooled and treated with a solution of 20.2 g. (0.107 mole) of tosyl chloride in 100 ml. of dry pyridine. The mixture is stirred at 25° C. for three days, poured into 800 ml. of water and extracted with ether. The combined ether extracts are washed with dilute hydrochloric acid and then with water, dried, filtered and evaporated to yield 3-methoxy-α-methyl-N-(2,2-dimethoxyethyl)-N-tosyl-benzylamine.

A mixture of 39.3 g. (0.1 mole) of 3-methoxy-α-methyl-N-(2,2-dimethoxyethyl)-N-tosyl-benzylamine, one liter of dioxane and 80 ml. of 6 N hydrochloric acid is refluxed for six hours and allowed to stand for sixteen hours. The mixture is poured into two liters of water and extracted with ether. The aqueous phase is made alkaline with concentrated ammonium hydroxide and extracted with chloroform. The chloroform extract is washed, dried and evaporated to yield 7-methoxy-1-methylisoquinoline.

Following the procedures of Example 8, the above isoquinoline is converted to 9-methyl-[1,2,3]thiadiazolo-[5,4-h]-6,7,8,9-tetrahydroisoquinoline hydrochloride.

EXAMPLE 10

A solution of 13.6 g. (0.1 mole) of 3-methoxybenzylamine and 11.8 g. (0.1 mole) of pyruvaldehyde dimethyl acetal in 30 ml. of toluene is refluxed for two hours and water formed in the reaction is collected in a Dean-Stark trap. The mixture is evaporated to yield the imine.

A mixture of 2.4 g. (0.01 mole) of the imine and 0.08 g. of platinum oxide in 200 ml. of ethyl acetate is reduced in a hydrogen atmosphere to yield 3-methoxy-N-[2-(1,1-dimethoxypropyl)]benzylamine.

Following the procedures of Example 9, 3-methoxy-N-[2-(1,1-dimethoxypropyl)]benzylamine is converted to 7-methyl[1,2,3]thiadiazolo[5,4-h]-6,7,8,9-tetrahydroisoquinoline hydrochloride.

EXAMPLE 11

A solution of 1.9 g. (0.01 mole) of [1,2,3]thiadiazolo[4,5-h]-6,7,8,9-tetrahydroisoquinoline and 4 ml. of 37% aqueous formaldehyde in 15 ml. of acetonitrile is treated with 1 g. (0.016 mole) of sodium cyanoborohydride. The reaction mixture is stirred for fifteen minutes and then glacial acetic acid is added dropwise until the solution is neutral on wet pH paper. Stirring is continued for an additional forty-five minutes, acetic acid being added as needed to maintain the pH near neutrality. The solvent is evaporated, the residue is taken up in 2 N aqueous potassium hydroxide and extracted with ether, which is washed, dried and evaporated to yield 8-methyl-[1,2,3]thiadiazolo[4,5-h]-6,7,8,9-tetrahydroisoquinoline.

EXAMPLE 12

Following the procedure of Example 2, 5-aminoisoquinoline and 6-aminoisoquinoline are converted, respectively, to 5-chloro-[1,2,3]thiadiazolo[4,5-f]-6,7,8,9-tetrahydroisoquinoline and [1,2,3]thiadiazolo[5,4-f]-6,7,8,9-tetrahydroisoquinoline.

EXAMPLE 13

Following the procedure of Example 2, 7-amino-8-trifluoromethylisoquinoline and 7-amino-8-chloroisoquinoline are converted to 4-trifluoromethyl-[1,2,3]thiadiazolo[5,4-g]-5,6,7,8-tetrahydroisoquinoline and 4-chloro-[1,2,3]thiadiazolo[5,4-g]-5,6,7,8-tetrahydroisoquinoline, respectively.

EXAMPLE 14

2-Acetyl-6-chloro-7-nitro-1,2,3,4-tetrahydroisoquinoline and 2-acetyl-7-chloro-6-nitro-1,2,3,4-tetrahydroisoquinoline are reduced with sodium hydrosulfite by the procedure of Example 1 to yield: 2-acetyl-7-amino-6-chloro-1,2,3,4-tetrahydroisoquinoline and 2-acetyl-6-amino-7-chloro-1,2,3,4-tetrachloroisoquinoline which are diazotized and neutralized following the procedure of Example 6 to yield: [1,2,3]-oxadiazolo[5,4-g]-5,6,7,8-tetrahydroisoquinoline and [1,2,3]-oxadiazolo[4,5-g]-5,6,7,8-tetrahydroisoquinoline.

EXAMPLE 15

| Ingredients | Amounts |
| --- | --- |
| [1,2,3]Thiadiazolo[5,4-h]-6,7,8,9-tetrahydroisoquinoline hydrochloride | 150 mg. |
| Lactose | 350 mg. |

The ingredients are mixed and filled into a hard gelatin capsule.

EXAMPLE 16

| Ingredients | Amounts |
| --- | --- |
| [1,2,3]Oxadiazolo[5,4-h]-6,7,8,9-tetrahydroisoquinoline | 200 mg. |
| Calcium sulfate dihydrate | 150 mg. |
| Sucrose | 25 mg. |
| Starch | 15 mg. |
| Talc | 5 mg. |
| Stearic Acid | 3 mg. |

The calcium sulfate dihydrate, sucrose and the tetrahydroisoquinoline are thoroughly mixed and granulated with 10% gelatin solution. The wet granules are screened, dried and then mixed with the starch, talc and stearic acid, screened and compressed into a tablet.

One tablet is administered three times a day.

What is claimed is:

1. A chemical compound of the formula selected from the group consisting of:

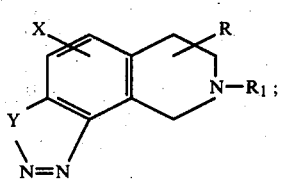

Formula I

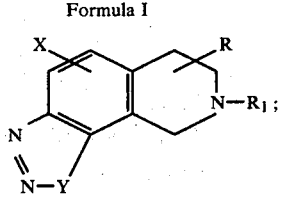

Formula II

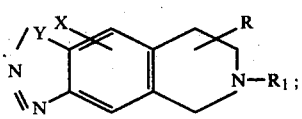

Formula III

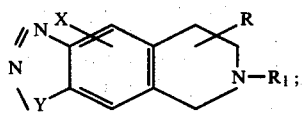

Formula IV

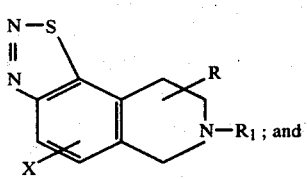

Formula V

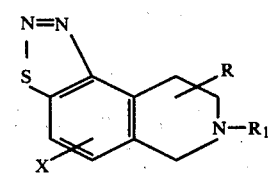

Formula VI in which:

Y is sulfur or oxygen;

when Y is sulfur, X is hydrogen, halogen, or trifluoromethyl, and R and $R_1$ are hydrogen or lower alkyl of from one to three carbon atoms; and when Y is oxygen, X, R and $R_1$ are hydrogen; or a pharmaceutically acceptable acid addition salt thereof.

2. A chemical compound of claim 1 in which Y is sulfur.

3. A chemical compound of claim 1 in which Y is oxygen.

4. A chemical compound of claim 2 in which X, R and $R_1$ are hydrogen having the formula of I or II.

5. A chemical compound of claim 4 in which the compound is [1,2,3]-thiadiazolo[5,4-h]-6,7,8,9-tetrahydroisoquinoline.

6. A chemical compound of claim 4 in which the compound is [1,2,3]-thiadiazolo[4,5-h]-6,7,8,9tetrahydroisoquinoline.

7. A chemical compound of claim 2 in which X is halogen having the formula of I or II.

8. A chemical compound of claim 7 in which X is halogen, R and $R_1$ are hydrogen being the compound 5-chloro-[1,2,3]-thiadiazolo[4,5-h]-6,7,8,9tetrahydroisoquinoline.

9. A chemical compound of claim 2 in which X, R and $R_1$ are hydrogen having the formula of III or IV.

10. A chemical compound of claim 9 in which the compound is [1,2,3]-thiadiazolo[5,4-g]-5,6,7,8-tetrahydroisoquinoline.

11. A chemical compound of claim 10 in which X is trifluoromethyl, R and $R_1$ are hydrogen having the formula of III or IV.

12. A pharmceutical composition in dosage unit form for inhibiting phenylethanolamine N-methyltransferase comprising a pharmaceutical carrier and a chemical compound as defined in claims 1, 5 or 6 in an amount effective to inhibit said phenylethanolamine N-methyltransferase.

13. A method of inhibiting phenylethanolamine N-methyltransferase in the adrenal glands and simultaneously inhibiting the formation of epinephrine from norepinephrine in an animal which comprises administering to an animal requiring said inhibition an amount sufficient to produce said inhibition of a chemical compound as defined in claims 1, 5 or 6.

14. A method of inhibiting phenylethanolamine N-methyltransferase in the adrenal glands and simultaneously inhibiting the formation of epinephrine from norepinephrine in an animal which comprises administering to an animal requiring said inhibition a dosage unit containing from about 50 mg. to about 1000 mg. of a chemical compound as defined in claim 1.

* * * * *